United States Patent [19]
Houlihan et al.

[11] 3,996,286
[45] Dec. 7, 1976

[54] α-BROMO-PIVALOYL TOLUENES

[75] Inventors: William J. Houlihan, Mountain Lakes; Jeffrey Nadelson, Lake Parsippany, both of N.J.

[73] Assignee: Sandoz, Inc., E. Hanover, N.J.

[22] Filed: Sept. 18, 1975

[21] Appl. No.: 614,536

Related U.S. Application Data

[60] Division of Ser. No. 342,463, March 19, 1973, Pat. No. 3,919,309, which is a continuation-in-part of Ser. No. 281,916, Aug. 18, 1972, abandoned.

[52] U.S. Cl. .......................... 260/592; 260/465 R; 260/465 F; 260/465 G
[51] Int. Cl.$^2$ ......................................... C07C 49/80
[58] Field of Search ..................................... 260/592

[56] References Cited
UNITED STATES PATENTS
3,013,079  12/1961  Pearson .............................. 260/592

OTHER PUBLICATIONS
Hass et al., J. Amer. Chem. Soc., vol. 71, pp. 1767–1769 (1949).

*Primary Examiner*—Lewis Gotts
*Assistant Examiner*—Dolph H. Torrence
*Attorney, Agent, or Firm*—Gerald D. Sharkin; Robert S. Honor

[57] ABSTRACT

Acyl substituted phenyl alkanoic acids, e.g. p-pivaloyl phenyl acetic acid, are prepared by hydrolyzing p-pivaloyl phenyl acetonitriles and are useful as hypolipidemic agents.

1 Claim, No Drawings

α-BROMO-PIVALOYL TOLUENES

This application is a division of application Ser. No. 342,463, filed March 19, 1973, now U.S. Pat. No. 3,919,309, which in turn is a continuation-in-part of application Ser. No. 281,916, filed Aug. 18, 1972, now abandoned.

This application relates to acyl substituted phenyl alkanoic acids which exhibit hypolipidemic activity. In particular, it relates to substituted phenyl alkanoic acids, pharmaceutically acceptable salts, their preparation and intermediates thereof.

The compounds of this invention may be represented by the formula:

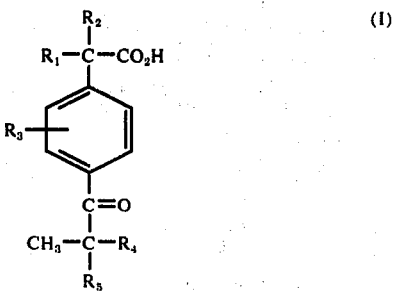

where
$R_1$ and $R_2$ each independently, represent hydrogen or lower alkyl having 1 to 2 carbon atoms, i.e. methyl or ethyl, and
$R_3$ represents hydrogen, halo having an atomic weight of about 19 to 36, and straight chain lower alkoxy, i.e., straight chain alkoxy having 1 to 4 carbon atoms, e.g., methoxy, ethoxy, isopropoxy or the like, and
$R_4$ and $R_5$ each independently, represent alkyl having 1 or 2 carbon atoms.

The compounds of formula (I) are prepared according to the following reaction scheme:

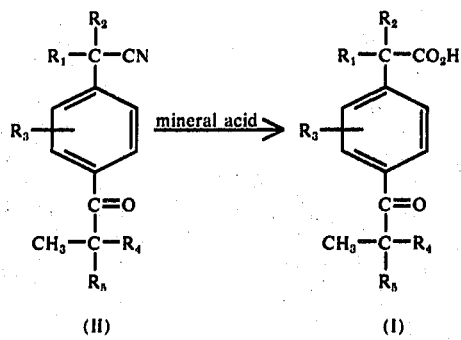

where $R_1$, $R_2$, $R_3$, $R_4$, and $R_5$ are as set out above.

The compounds of formula (I) are prepared by hydrolyzing compounds of formula (II) with aqueous mineral acids. When $R_1$ is hydrogen or halo, it is preferred that concentrated mineral acid be used. When $R_1$ is lower alkoxy, it is preferred that a dilute mineral acid be employed. The acid can be hydrochloric acid, sulfuric acid, phosphoric acid and the like. The particular acid used is not critical but hydrochloric acid is preferred. The aqueous solvent can be water or a mixture of water and a water soluble organic solvent, e.g., the lower alkanols. The preferred solvent is water, although the particular solvent used is not critical. The temperature of the reaction is also not critical, but it is preferred that the reaction be carried out at the reflux temperature of the solvent. For optimum results the reaction is run for about 12 to 72 hours, preferably 40 to 50 hours. The product is recovered by conventional techniques, e.g., recrystallization.

The compounds of formula (II) where $R_1$ and $R_2$ each represent lower alkyl are prepared according to the following reaction scheme:

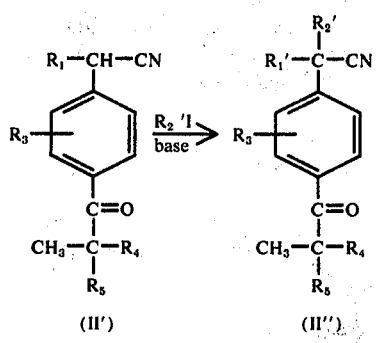

where
$R_1'$ and $R_2'$ are each independently lower alkyl, and
$R_1$, $R_3$, $R_4$ and $R_5$ are as set out above,
provided that when $R_1$ is hydrogen, $R_1'$ and $R_2'$ each represent the same lower alkyl.

The compounds of formula (II'') are prepared by reacting a compound of the formula (II') with an alkyl iodide such as methyliodide in the presence of an inorganic base and an inert organic solvent. Suitable strong bases which may be employed include the alkali metal amides such as potassium amide and the alkali metal hydrides such as sodium hydride or potassium hydride. The particular base used is not critical but sodium amide is preferred. The preferred solvents are dimethylacetamide, tetrahydrofuran, ether or liquid ammonia, the latter being especially preferred. The temperature of the reaction is not critical, but it is preferred that the reaction be carried out between about $-100°$ to $-50°$ C., especially $-80°$ to about $-70°$ C. The reaction is run from about 1 to 6 hours, preferably from about 2.5 to 3.5 hours. The product is recovered using conventional techniques, e.g. filtration.

The compounds of formula (II') can be prepared according to the following reaction scheme:

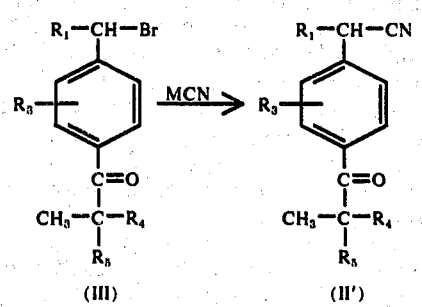

where
M repesents an alkali metal, preferably sodium or potassium and
$R_1$, $R_3$, $R_4$ and $R_5$ are as set out above.

The compounds of formula (II') are prepared by treating compounds of formula (III) with an alkali metal cyanide such as sodium cyanide, potassium cyanide, and the like, preferably potassium cyanide, in the presence of an aqueous organic solvent. The preferred solvents are the aqueous-lower alkanols such as water and methanol, ethanol and the like, and water-dioxane, although anhydrous dimethylsulfoxide can also be employed. The temperature of the reaction is not critical but it is preferred that the process be carried out at a temperature between about 40° to 120° C, especially the reflux temperature of the system. For optimum results, the reaction is run for about 1-10 hours; preferably 3 to 5 hours. The product is recovered by conventional techniques, e.g., evaporation.

The compounds of formula (III) are prepared according to the following reaction scheme:

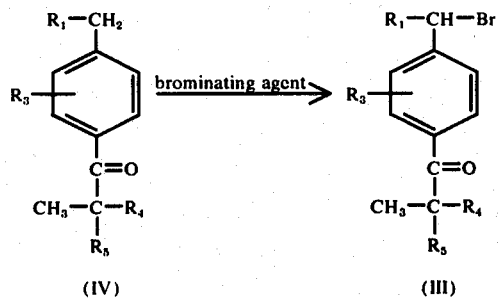

where
$R_1$, $R_3$, $R_4$, and $R_5$ are as set out above.

The compounds of formula (III) are prepared by treating a compound of formula (IV) with a brominating agent in the presence of an inert organic solvent and free radical initiator. The brominating agent which can be used is bromine, N-bromosuccinimide, N-bromo phthalamide, N-bromo-acetamide and the like. The particular agent used is not critical, but N-bromosuccinamide is preferred. In the preferred process, the free radical initiator used is an organic or inorganic peroxide, especially benzoyl peroxide. The reaction can also be carried out under ultraviolet light. Although the particular solvent used is not critical, the preferred solvents are the halogenated hydrocarbons such as methylene dichloride, chloroform, carbon tetrachloride and the like, although the aromatic hydrocarbons such as benzene can also be employed. The temperature of the reaction is not critical, but reflux temperature of the solvent is preferred. For optimum results, the reaction is run for about 12 to 48 hours; preferably 18 to 25 hours. The product is recovered by conventional techniques, e.g., crystallization.

Many of the compounds of formula IV are known and may be prepared by methods described in the literature. The compounds of formula IV not specifically disclosed may be prepared by analogous methods from known starting materials.

The compounds of formula (I) are useful because they possess pharmacological activity in animals, particularly as hypolipidemic agents and the compounds are especially useful as hypocholesterolemic and hypotriglyceridemic agents as indicated by the fall in cholesterol and triglyceride levels in male albino Wistar rats weighing 110–130 g. initially. The rats are maintained on drug-free laboratory chow diet for seven days and then divided into groups of 8 to 10 animals. Each group with the exception of the control is then given orally 30 milligrams per kilogram of body weight per diem of the compound for six days. At the end of this period, the animals are anesthetized with sodium hexobarbital and bled from the carotid arteries. Serum or plasma samples are collected, and 1.0 ml samples of the serum are added to 9.0 ml redistilled isopropanol. Two autoanalyzer cupsful of a mixture of zeolite-copper hydroxide and Lloydds reagent (Kessler, G., and Lederer, H., 1965, Technicon Symposium, Mediad Inc., New York, (345–347) are added, and the mixture is shaken for one hour. Cholesterol and triglyceride levels are determined simultaneously on the same sample by Technicon N 24 A (cholesterol) and N-78 (triglyceride) methodology. The mean total serum cholesterol levels are then computed and the hypocholesterolemic activity is expressed as the fall in cholesterol levels as a percentage of the control level. The change in serum triglyceride levels induced by the drug is computed as a percentage of the control triglyceride levels.

For such usage, the compounds (I) may be combined with a pharmaceutically acceptable carrier or adjuvant and may be administered orally or parenterally as such as admixed with conventional pharmaceutical carriers. They may be administered in such forms as tablets, dispersible powders, granules, capsules, syrups and elixirs and parenterally as solutions, suspensions, dispersions, emulsions and the like, e.g. a sterile injectable aqueous solution. The dosage will vary depending upon the mode of administration utilized and the particular compound employed.

The compounds of formula (I) may be similarly administered in the form of their non-toxic pharmaceutically acceptable salts. Such salts possess the same order of activity as the free base, and are readily prepared by reacting the base with an appropriate hydroxide or oxide and, accordingly, are included within the scope of this invention. Representative of such salts are the alkali metal salts, e.g. sodium, potassium and the like, and alkaline earth metal salts such as magnesium, calcium and the like.

The hypolipidemic effective dosage of compounds (I) employed in the alleviation of lipidemia may vary depending on the particular compound employed and the severity of the condition being treated. However, in general, satisfactory results are obtained when the compounds of formula (I) are administered at a daily dosage of from about 1.0 milligrams to about 250 milligrams per kilogram of animal body weight, preferably given in divided doses two to four times a day, or in sustained release form. For most large mammals, the total daily dosage is from about 75 milligrams to about 2500 milligrams. Dosage forms suitable for internal use comprise from about 18.5 to about 1250 milligrams of the active compound in intimate admixture with a solid or liquid pharmaceutically acceptable carrier or diluent.

A representative formulation suitable for oral administration 2 to 4 times a day for the treatment of lipidemia is a capsule prepared by standard encapsulating techniques which contains the following:

| Ingredients | Weight (mg) |
| --- | --- |
| p-pivaloyl phenyl acetic acid | 100 |
| inert solid diluent (starch, lactose, kaolin). | 200 |

EXAMPLE I

α-bromo-p-pivaloyl toluene.

To a suspension of 28.5 g (1.17 g. atoms) magnesium turnings in 150 ml tetrahydrofuran under a nitrogen atmosphere there is added 10 ml (1.17 mole) of 4-bromotoluene in 650 ml dry tetrahydrofuran, the reaction is started and the remainder of the bromotoluene solution is added dropwise at a rate that maintains a moderate reflux. After the addition is complete, the mixture is refluxed for an additional 1 1/2 hours. The resulting Grignard solution is added dropwise to a cold solution of 128.0 g. pivaloyl chloride (1.06 mole) in 500 ml dry tetrahydrofuran at a rate that maintains the temperature at 0° to −5° C. The solution is stirred for an additional 1 1/2 hours at 0° and then at room temperature for 18 hours. The mixture is then cooled to 0° and hydrolyzed by the addition of 100 ml 2N hydrochloric acid. The layers are separated and 200 ml of ether is added to the organic phases which is then washed respectively with 100 ml 2N hydrochloric acid, 100 ml. 10% sodium bicarbonate solution and 100 ml saturated sodium chloride. The resulting layer is dried over anhydrous sodium sulfate, filtered, and the solvent is removed in vacuo to give p-pivaloyl toluene (b.p. 80°–84° C/0.7 mm, $n^{21}$=1.5108). A mixture of 156.3 g. (0.886 mole) of the resulting p-pivaloyl toluene is then added to 157.8 g. (0.886 mole) N-bromosuccinimide, 4.0 g (0.016 mole) benzoyl peroxide and 150 ml. carbon tetrachloride and heated at reflux for 18 hours. The mixture is cooled and filtered and the resulting precipitate is washed with carbon tetrachloride. The solvents are removed in vacuo and the resulting oil is distilled in vacuo to give α-bromo-p-pivaloyl toluene (b.p. 124° – 132°/0.7 mm, $n^{22}$=1.5546-V.P.C. 96% monobromo 4%-dibromo).

Following the above procedure and using in place of 4-bromotoluene equivalent amount of:
a. 4-bromo-2-chlorotoluene,
b. 4-bromo-2-methoxytoluene,
c. 4-bromo-ethylbenzene, or
d. 4-bromo-2-fluorotoluene, there is obtained
a. α-bromo-2-chloro-4-pivaloyl toluene,
b. α-bromo-2-methoxy-4-pivoloyl toluene,
c. α-bromo-α-methyl-4-pivaloyl toluene, or
d. α-bromo-2-fluoro-4-pivaloyl toluene, respectively.

p-pivaloyl phenyl acetonitrile

A solution of 34.3 g (0.700 mole) sodium cyanide in 40 ml of water is warmed to 50° C and a solution of α-bromo-p-pivaloyl toluene in 85 ml ethanol is then added dropwise at such a rate as to maintain the temperature at 50° C. After the addition is complete the mixture is refluxed for four hours. The excess ethanol is removed in vacuo and the resulting residue is treated with ether/water. The layers are separated and the ether is washed with cold 50% sulfuric acid, water and sodium bicarbonate, then the ether layer is dried over anhydrous magnesium sulfate, filtered and evaporated in vacuo. The residue is distilled in vacuo to give p-pivaloyl phenyl acetonitrile (b.p. 143–148° C/0.75 mm $n^{22}$=1.5244.)

Following the above procedure and using in place of α-bromo-p-pivaloyl toluene an equivalent amount of
a. α-bromo-2-chloro-4-pivaloyl toluene,
b. α-bromo-2-methoxy-4-pivaloyl toluene, or
c. α-bromo-α-methyl-4-pivaloyl toluene, or
d. α-bromo-2-fluoro-4-pivaloyl toluene, there is obtained
a. 2-chloro-4-pivaloyl phenyl acetonitrile,
b. 2-methoxy-4-pivaloyl phenyl acetonitrile,
c. 2-(p-pivaloyl phenyl) propionitrile, or
d. 2-fluoro-4-pivaloyl phenyl acetonitrile, respectively.

p-pivaloyl phenyl acetic acid.

To a flask equipped with a stirrer, dropping funnel and condenser there is added 50.0 g (0.25 mole) p-pivaloyl phenyl acetonitrile to 1 liter concentrated hydrochloric acid which is then refluxed for 48 hours. The resultant precipitate is filtered, dissolved in chloroform, and washed with 2N sodium hydroxide. The basic aqueous phase is separated from the organic phase, cooled and acidified with concentrated hydrochloric acid and the resulting solid is then recrystallized from hot benzene to give p-pivaloyl phenyl acetic acid, m.p. (111°–112° C).

Following the above procedure and using in place of p-pivaloyl phenyl acetonitrile and equivalent amount of
a. 2-chloro-4-pivaloyl phenyl acetonitrile,
c. 2-(p-pivaloyl phenyl) propionitrile, or
d. 2-fluoro-4-pivaloyl phenyl acetonitrile, there is obtained
a. 2-chloro-4-pivaloyl phenyl acetic acid,
b. 2-(p-pivaloyl phenyl) propionic acid, or
d. 2-fluoro-4-pivaloyl phenyl acetic acid, respectively.

Again following the above procedure and using in place of p-pivaloyl phenyl acetonitrile an equivalent amount of 2-methoxy-4-pivaloyl phenyl acetonitrile in the presence of a dilute hydrochloric acid in place of concentrated hydrochloric there is obtained 2-methoxy-4-pivaloyl phenyl acetic acid.

The p-pivaloyl phenyl acetic acid of this example is an effective hypolipidemic agent when orally administered to an animal suffereing from lipidemia at a dosage of from about 50 to 250 milligrams four times per day.

2-methyl-2-(p-pivaloyl phenyl) propionic acid

To a suspension of 4.68 g. (0.12 mole) of sodium amide in 100 ml. of liquid ammonia at −78° C. there is added dropwise for about 30 minutes a solution of 6.03 g. (0.03 mole) p-pivaloyl phenyl acetonitrile and 17 g. (0.12 mole) of methyl iodide in 100 ml. of dry ether. The resulting mixture is stirred for 3 hours at −78° C. and then there is added 6.5 g. of solid ammonium chloride, and the excess ammonia is allowed to evaporate. Ether and water are added to the residue and the layers are separated. The organic layer is washed with brine, decolorized with charcoal, dried over anhydrous magnesium sulfate, filtered and evaporated to give an oil. The crude oil is refluxed with 100 ml. of 50% concentrated sulfuric acid for 72 hours. The resulting mixture is cooled and extracted with ether. The excess ether is extracted with 2N sodium hydroxide, and the basic solution is charcoaled, made acidic with concentrated hydrochloric acid and extracted with methylene chloride. The excess methylene chloride is washed with brine, dried over anhydrous magnesium sulfate, filtered and evaporated. The residue is recrystallized from petroleum ether/ether to give 2-methyl-2-(4-pivaloyl phenyl) propionic acid; m.p. 128°–130° C.

Following the above procedure and using in place of p-pivaloyl phenyl acetonitrile an equivalent amount of
a. 2-chloro-4-pivaloyl phenyl acetonitrile, or
b. 2-methoxy-4-pivaloyl phenyl acetonitrile, or c. 2-fluoro-4-pivaloyl phenyl acetonitrile, there is obtained a. 2-methyl-2-(2-chloro-4-pivaloyl phenyl) propionic acid, b. 2-methyl-2-(2-methoxy-4-pivaloyl phenyl) propionic acid, or c. 2-methyl-2-(2-fluoro-4-pivaloyl phenyl) priopionic acid, respectively.

What is claimed is:

1. A compound of the formula

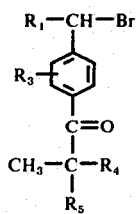

where

R₁ represents hydrogen, or alkyl of 1 to 2 carbon atoms, and

R₃ represents hydrogen, halo having an atomic weight of about 19 to 36 or straight chain lower alkoxy, and R₄ and R₅ each independently, represent alkyl having 1 or 2 carbon atoms.

* * * * *